United States Patent [19]

Whigham et al.

[11] Patent Number: 4,821,724

[45] Date of Patent: Apr. 18, 1989

[54] PACING PULSE COMPENSATION

[75] Inventors: Robert H. Whigham, Aurora; Tibor A. Nappholz, Englewood, both of Colo.

[73] Assignee: Telectronics N.V., Curacao, Netherlands Antilles

[21] Appl. No.: 891,479

[22] Filed: Aug. 1, 1986

[51] Int. Cl.4 .......................... A61N 1/00; H05G 00/00
[52] U.S. Cl. ............................ 128/419 P; 128/419 PG
[58] Field of Search ....... 128/419 P, 419 PG, 419 PS, 128/419 PT

[56] References Cited

U.S. PATENT DOCUMENTS

| 3,835,865 | 9/1974 | Bowers | 128/419 PG |
| 3,985,142 | 10/1976 | Wickham | 128/419 PG |
| 4,114,627 | 9/1978 | Lewyn et al. | 128/419 PG |
| 4,236,522 | 12/1980 | McDonald | 128/419 PG |
| 4,373,531 | 2/1983 | Wittkampf et al. | 128/419 PG |
| 4,592,360 | 6/1986 | Lesnick | 128/419 PG |
| 4,705,043 | 11/1987 | Imran | 128/419 PG |

Primary Examiner—Francis Jaworski
Assistant Examiner—George Manuel
Attorney, Agent, or Firm—Gottlieb, Rackman & Reisman

[57] ABSTRACT

A pacemaker which generates a triphasic stimulus; the first and third phases are positive pulses, and the second is the negative stimulus. After-potentials are so low that reliable sensing of evoked signals are possible. The rapidity of the charge balancing is not affected by the stimulus amplitude because the relative amplitudes of the three phases are maintained independent of the stimulus amplitude.

28 Claims, 6 Drawing Sheets

FIG. 3

| | SW 1 | SW 2 | SW 3 | SW 4 | SW 5, 6, 7, 19, 20 | SW 8 | SW 9 | SW 10 | SW 11, 13 | SW 12 | SW 14, 16 | SW 15 | SW 17, 18 | SW 21 | SW 22 |
|---|---|---|---|---|---|---|---|---|---|---|---|---|---|---|---|
| ECG Processing | | | U | B | C | | | | | | | | | | |
| Blanking | | | | | | | | | | | | | | | |
| Precharge | U | B | | | | | | | | | | | | | |
| Stimulus | U | B | | | | C | | | | | | | | | |
| Active Postcharge | U | B | | | | | C | C | C | C | C | | C | | |
| Passive Postcharge | U | B | | | | | | C | C | C | | | C | | |
| Alert Drive High | C | | | | | | | C | C | C | | M | N | C | |
| Alert Drive Low | C | | | | | | | C | C | C | | M | N | C | |
| Sensor Drive Case | C | | | | | | | | | | | | C | | C |
| Sensor Drive Ring | | | C | | | | | | | | | | | | |

C = Closed

M = Closed when 32K_CLOCK is high

N = Closed when 32K_CLOCK is low

U = Closed if unipolar pacing (SW1) or sensing (SW3)

B = Closed if bipolar pacing (SW2) or sensing (SW4)

ECG PROCESSING

BLANKING

STIMULUS

PRECHARGE

PASSIVE POSTCHARGE

ACTIVE POSTCHARGE

PACING PULSE COMPENSATION

This invention relates to pacemakers, and more particularly to pacemakers which allow sensing of evoked potentials very soon after the generation of a pacing stimulus even when the same electrode is used for pacing and sensing.

The generation of any heart pacing stimulus gives rise to the storage of charges in body tissues. Until those charges dissipate appreciably, it is usually impossible to sense electrical activity. This is especially true if the same electrode is used for both pacing and sensing. The beating of the heart gives rise to potentials which can be sensed. However, until the charges resulting from a pacing stimulus dissipate sufficiently, reliable sensing is impossible because the potentials arising from those charges are so much greater than those resulting from a heartbeat.

It is standard practice in the pacemaker art to blank for many milliseconds the sense amplifier connected to a lead over which a pacing stimulus is generated. This means that the sense amplifier cannot determine that the heart actually beat as a result of the stimulus. Similarly, in the case of a dual-chamber pacemaker, a ventricular blanking period is generally associated with the ventricular sense amplifier starting with the generation of an atrial stimulus; in this way, an atrial stimulus is not mistaken as a ventricular beat. Once again, until the charges associated with the atrial stimulus dissipate, ventricular sensing is not possible. It has long been a goal to shorten the blanking periods by speeding up the charge dissipation process, thus solving the "cross-talk" problem which is inherent in a dual-chamber pacemaker without impairing the sensing capability.

Toward this end, it is now common to provide what is known as active recharge. A typical pacemaker includes a coupling capacitor in the output circuit. Because the net current flow through a capacitor must be zero, the provision of AC coupling insures that there is no net charge delivered to the body tissues. The output capacitor is generally part of the pulsing circuitry. Charge is stored on the capacitor, and it is then delivered rapidly over the lead when a stimulus is required. The charge delivered then flows in the opposite direction through the capacitor until the charges in body tissues are dissipated. In order to speed up the charge neutralization, an "active" recharge circuit can be used to connect the output capacitor through a transistor switch to a potential source. This causes a larger reverse current to flow through the capacitor, and the charges stored in the body tissues dissipate more rapidly. Negative pulses are most often used to stimulate the heart. Thus with an active recharge circuit, the pacing cycle consists of a negative pulse followed by a positive pulse.

A recent development is that of providing a precharge positive pulse in addition to a postcharge positive pulse. This technique is described in U.S. Pat. Nos. 4,343,312 and 4,373,531. The total charge delivered during the two positive pulses equals the charge delivered during the negative pulse in the opposite direction; in this way the net charge is zero. Although it is not described in these two patents why the provision of a positive precharge pulse together with a positive postcharge pulse is better than the latter alone, even when the combined "area" under both pulses in the first case is equal to the "area" under the single pulse in the latter case, there is no question that the stored charges dissipate more rapidly. My analysis shows that the reason for this has to do with the space charges delivered by the electrode. The process can be thought of as three spherical wavefronts emanating from a point source. The magnitudes of the wavefronts and their separations can be adjusted so that soon after the launching of the last wavefront, the net potential at the point source approaches zero. Unfortunately, the circuits disclosed as exemplary in the two above-identified patents can only be implemented in practice with difficulty.

It is an object of our invention to provide a pacing system which, with minimum controls, allows safe, reliable sensing of the capture of the heart (atrium or ventricle).

It is another object of our invention to provide a pacing system which allows the complex process of polarization elimination to be realized in integrated form.

It is another object of our invention to provide a pacing system in which single-ended or differential sensing of evoked potentials is accomplished by the same elements which eliminate the electrode polarization.

It is another object of our invention to provide a pacing system in which the balancing of electrode polarization is achieved with a single setting which is then independent of changes in pacing voltage amplitude.

It is still another object of our invention to eliminate "cross-talk" in a dual-chamber pacemaker without impairing the sensing capability.

The method of our invention, by which the afterpotential at a pacing electrode following the generation of a pacing stimulus is minimized, entails the use of a differential amplifier to sense cardiac activity. The pacemaker stimulating and reference electrodes are connected to the inputs of the amplifier. A triphasic stimulus is generated, with the first and third phases being of one polarity and the second being of the opposite polarity. The first and second phases are delivered through a capacitor and the voltage drives which are provided have amplitudes which are substantially proportional to each other. The first phase begins with a quiescent voltage across the capacitor. The third phase utilizes the voltage across the capacitor to drive a current through the capacitor and the stimulating electrode until the voltage across the capacitor equals the starting quiescent voltage.

This technique is to be distinguished from that disclosed, for example, in the above-identified patents. The prior art technique really works only in the case of steady-state pacing. At the start of each pacing cycle, there is some initial voltage across the output capacitor. If pacing pulses are continuously generated at a fixed rate, some steady-state condition is eventually reached with the capacitor voltage at the end of the cycle being equal to the capacitor voltage at the start of the cycle. The result is very fast charge balancing, as desired. But if the heart is not paced steadily, the capacitor voltage drops as the result of leakage through the capacitor and in the printed circuit board on which it is mounted. The result is that for the first number of cycles that the heart is paced, the charge balancing is not sufficient to allow the sensing of evoked potentials. In our invention, however, sensing of evoked potentials is possible the first time that the heart is paced, even if it has not been paced for hours before that, i.e., the advantages of the invention apply even to an isolated stimulus cycle. Capture of the heart can be sensed immediately, even following the generation of the first pacing pulse. Another difficulty with the prior art technique is that the charge balancing, and therefore the sensing of an evoked potential, is dependent upon the stimulus amplitude. As the amplitude is changed, for example, using a conventional external programmer, adjustments must be made to the charge balancing circuit. In our invention, the adjustment is automatic. More accurately, no adjustment need even be made.

Further objects, features and advantages of the invention will become apparent upon consideration of the following detailed description in conjunction with the drawing, in which:

FIG. 1 is a block diagram of an overall pacemaker in which the system of our invention may be incorporated;

FIGS. 2A and 2B, with FIG. 2A being placed to the left of FIG. 2B, depict the illustrative embodiment of our invention—the circuitry included in the sensing and polarization controller block 15 of FIG. 1;

FIG. 3 is a table which characterizes he operations of the switches of the circuit of FIGS. 2A and 2B;

Figure 1:
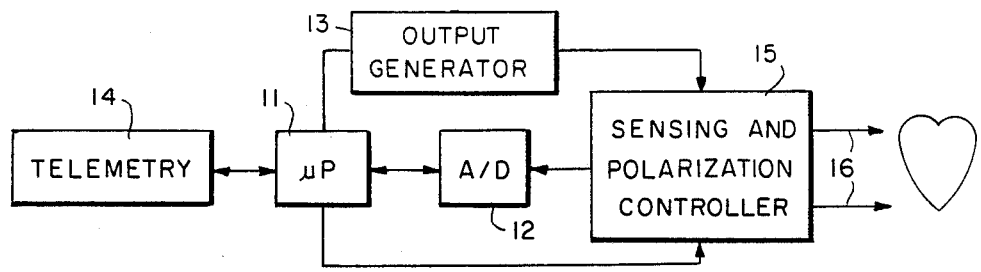

The pacemaker of FIG. 1 is depicted in a highly symbolic block-diagram form. Microprocessor 11 controls all of the other blocks. The telemetry block 14 is conventional in today's pacemakers, and allows both adjustment of pacemaker parameters from an external programmer, and the transmission of information from the pacemaker which is indicative not only of accumulated data, but even a signal representative of the instantaneous sense signal. Present-day sophisticated telemetry circuits allow for the interrogation of stored diagnostic data, and the derivation of real-time operational data.

The analog-to-digital block 12 is provided with a signal called ANLG_CMP from the sensing and polarization controller 15. The ANLG_CMP signal is a 2-level waveform at the Q output of flip-flop 52 in FIG. 2B. As will be described, the sequence of bits which comprise the signal represents increases and decreases in the sense signal. The A/D block 12 acts on this signal, under control of the microprocessor, to derive information about the sense signal. The ANLG_CMP waveform, of course, is derived in accordance with operations of block 15 on the two leads 16 which are extended to the heart, as will be described.

Figure 2A:
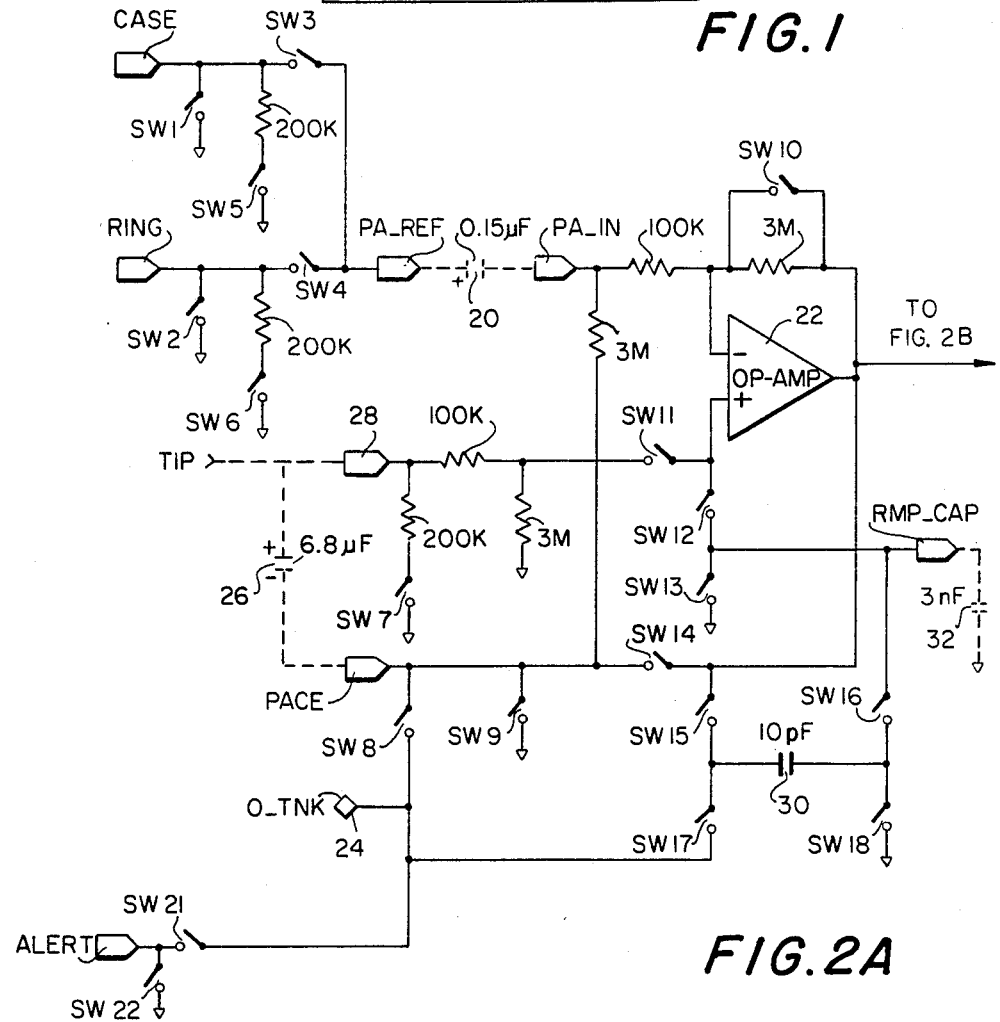
Figure 2B:
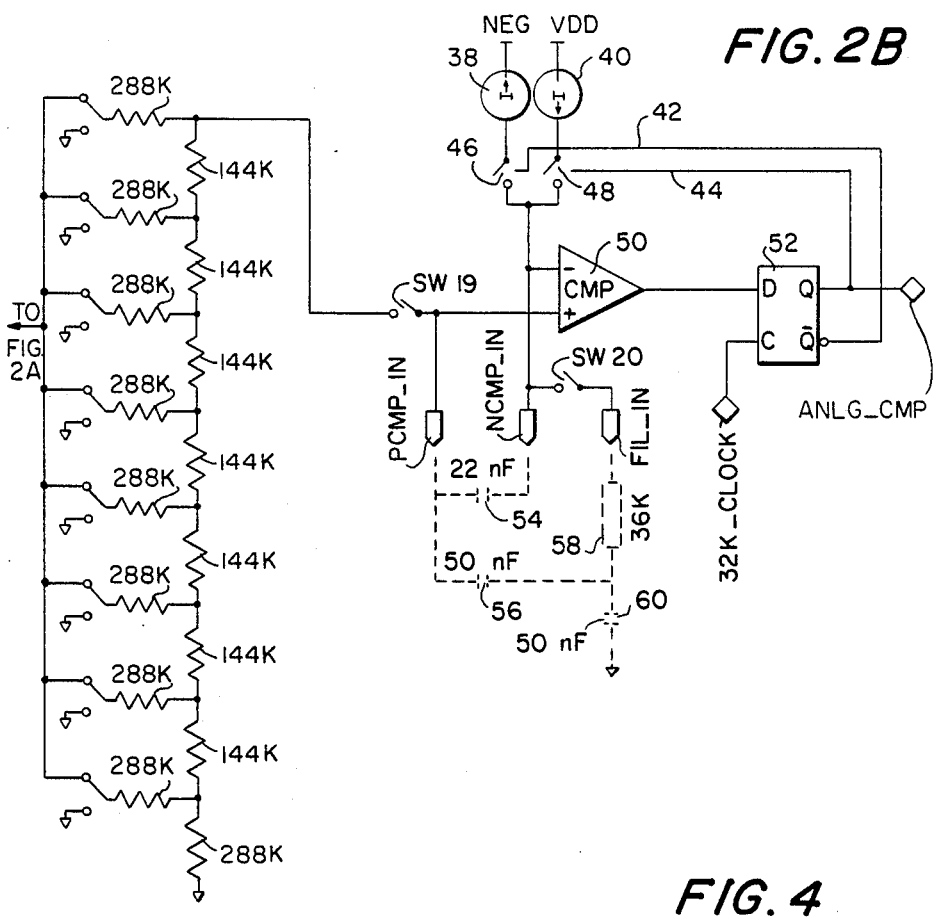

The microprocessor has a direct connection to the sensing and polarization controller block 15, and the signals over this direct link control the various switches depicted in FIGS. 2A and 2B. In addition, output generator 13 provides a potential over its output lead extended to block 15. In connection with FIGS. 2A and 2B, the potential is labeled 0_TNK. This potential represents the magnitude of the negative phase of the stimulating pulse. As will be described, the circuitry of FIGS. 2A and 2B which corresponds to block 15 of FIG. 1 permits rapid charge balancing independent of the magnitude of the 0_TNK signal.

The circuit of FIGS. 2A and 2B is shown in solid lines and dashed lines. The solid lines represent those elements included in the integrated circuit which are at the heart of block 15 of FIG. 1. The dashed lines are the external components which are too large to be fabricated on the chip. Connections to the integrated circuit are made via the pins which are depicted in the drawing. For example, at the top of FIG. 2A a capacitor 20 is shown in dashed lines. This 0.15 uF capacitor is too large to be fabricated on the integrated circuit. For this reason it is in the form of an external component connected across integrated circuit pins PA_REF and PA_IN (which labels represent a preamplifier reference pin and a pre-amplifier input pin).

Before describing the circuit operation, it will be helpful to make a few general remarks. There are 22 switches labeled SW1 through SW22. Depending on the mode in which block 15 of FIG. 1 is being operated, as determined by microprocessor 11, some of the switches are open and the others are closed. FIG. 3 depicts those switches which are open and closed in each mode of operation. It is to be understood that all of the switches are active circuits on the integrated circuit chip.

Referring to FIG. 2A, pin 28 is connected to the tip lead, and the PACE pin is connected through external capacitor 26 to the tip lead. The tip is the lead connected to the electrode in the heart which provides the negative stimulus. It will be noted that there are two pins labeled CASE and RING. If a bipolar lead is used, the indifferent electrode can be either the ring or the case. If a unipolar electrode is used, then the indifferent electrode must be the case. The pin labeled CASE is connected electrically to the case; the pin labeled RING is connected to the ring electrode only if a bipolar lead is employed. In the event a bipolar lead is used, it is the positions of switches 1 through 4 which determine which of the two possible indifferent electrodes (CASE or RING) is operative.

It should be noted that, as depicted in the table of FIG. 3, switches 5, 6, 7, 19 and 20 are all open or closed together. The first three switches control the connection of the two possible anodes (case or ring) and the stimulating lead (tip) to the reference ground. During ECG Processing (sensing), all three of these switches are closed, as are switches 19 and 20. The latter two switches are closed in order that a delta modulator (on FIG. 2B) function, and the former three switches are closed to connect each of the three inputs through a 200K resistor to reference ground. At all other times, according to the table of FIG. 3, the five switches are open. Switches 19 and 20 are held open so that the delta modulator function as a sample-and-hold circuit. Switches 5, 6 and 7 are similarly held open because it is not desired that current flow through the case, ring or tip and the respectively connected 200K resistors to reference ground. During the various phases involved in pacing, and even in the alert and sensor drive modes, current pulses are applied by the pacemaker and it is undesirable for any of the current to be allowed to flow through the 200K resistors. The provision of separate switches for the case and ring inputs allows a dual-chamber pacemaker to be made, using duplicates of the circuits of FIGS. 2A and 2B, but to even have the different chambers paced in different modes—unipolar or bipolar. [Using two of the circuits in a dual-chamber pacemaker, switches 19 and 20 in one would be open even when a pacing stimulus is generated by the other; the object is to monitor the electrogram signal for each chamber only when neither chamber is being paced so that it is only cardiac activity which is analyzed.]

Capacitor 20 is a standard coupling capacitor which is used to block DC on the electrodes and to prevent the DC offset voltage of operational amplifier 22 from being amplified. Operational amplifier 22 has a gain of 30 when switch 10 is open, this being the ratio of the feedback resistor, between the output of the amplifier and the minus input, to the input impedance connected to the minus input. The operational amplifier functions to equalize the two signals at its minus and plus inputs. However, in practice it is not possible to achieve this, and there is some offset voltage across the plus and minus inputs of operational amplifier 22. This offset voltage is stored on capacitors 20 and 26.

Figure 4:
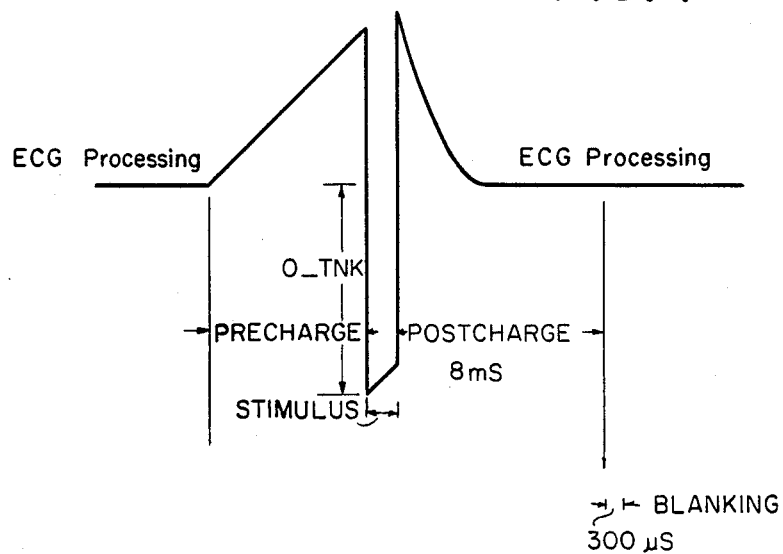
FIG. 4 depicts the form of the triphasic pacing pulse generated by the circuit of FIGS. 2A and 2B.

Capacitor 26 is the standard-type AC coupling capacitor for generating the stimulus. FIG. 4 depicts the form of the triphasic pacing stimulus as it appears at the PACE pin. The positive pre-charge pulse is in the form of a ramp. While a ramp is not essential, it is preferred because it has been shown empirically that the operation of the circuit is less dependent on the stimulus amplitude when a ramp precharge pulse is used rather than a rectangular precharge pulse. Also, it is commonly accepted that a sharp positive pulse is more likely to trigger tachycardia if it is applied during a T wave. However, the present invention is not limited to the use of a ramp potential for the precharge pulse. Similarly, it is known that a beat can be triggered with a positive pulse, and therefore the polarities of the three phases of the stimulus shown in FIG. 4 can be reversed. However, it is preferred that the middle phase be negative, as shown, because it is generally acknowledged that less energy is required to pace the heart if a negative stimulus is used.

The amplitude of the stimulus is the magnitude of the vertical line in FIG. 4 between the horizontal base line and the lowermost extent of the negative stimulus. This magnitude is labeled 0_TNK, and it is determined by the magnitude of the potential at node 24. This potential may vary between 0 and 7.5 volts in the illustrative embodiment of the invention. [Node 24 is not shown as a pin. The reason for this is that in the actual implementation of the system of FIG. 1, it is not necessary that the separations between blocks 12, 13 and 15 be exactly as shown. The 0_TNK potential at node 24 may be derived from still other circuits included in the same chip which contains the circuit of FIGS. 2A and 2B, but these elements are not important for an understanding of the present invention. Therefore, the operative input is simply labeled 0_TNK at a node 24, without paying concern to the additional elements connected between the node and input pins. Similarly, in the actual implementation of the invention, the circuitry at the far right of FIG. 2B, including comparator 50 and current sources 38 and 40, may be actually included in A/D block 12 of FIG. 1. The invention has nothing to do with the particular circuit partitioning which is employed.]

The 0_TNK value can be fixed by an external programmer. Alternatively, energy can be conserved if the stimulus amplitude is caused by the microprocessor to track the threshold. How the 0_TNK magnitude is determined has no bearing on use of the present invention. It is assumed, however, that the 0_TNK potential is derived from a capacitor. In such a case, the capacitor would discharge slightly during application of the negative stimulus. That is why FIG. 4 shows the negative pulse decreasing slightly in magnitude during the course of the stimulus.

The waveform of FIG. 4 is not drawn to scale. The precharge period has a duration of about 3 milliseconds, the postcharge interval has a duration of about 8 milliseconds, the width of the negative stimulus is about 0.5 milliseconds, and a blanking interval of 300 microseconds (to allow the circuit to settle after switching) follows the overall cycle. The waveform represents the potential at the PACE pin.

Capacitor 32, connected to the RMP_CAP pin, serves to generate the ramp waveform which controls the shape of the precharge pulse shown in FIG. 4. Although it is only 3 nF in magnitude, it is still too large to be integrated and it is therefore an external component. Capacitor 30, which serves as a charge pump, as will be described, is small enough to be integrated.

The ALERT pin at the lower left of FIG. 2A is used to drive a piezoelectric crystal which serves as a sonic alarm. The ALERT circuit has no bearing on the present invention, and is shown only because it is part of the integrated circuit. The patient actually hears a beep, and is warned to seek medical attention. The physician programs the microprocessor to trigger the alarm under specified conditions. To actually sound the alarm, the microprocessor alternately operates switches 21 and 22. In the illustrative embodiment of the invention, it is the 0_TNK voltage at node 24 which actually drives the crystal. Referring to FIG. 3, it will be seen that when the ALERT pin is to be driven high, switch 21 is closed, and when it is to be driven low, switch 22 is closed so that the pin can be connected to circuit ground. Switch 1 is closed during the alert sequence; the case is grounded and thus the return path for the current is through the case. All other switches (except switches 11, 13, 17 and 18—to be discussed below) are open; in the table of FIG. 3, the absence of a code letter is indicative of the respective switch being open.

As far as the table of FIG. 3 itself is concerned, the switch conditions which are represented will be understood as the detailed operation of the system is described. However, the various modes of operation should be appreciated before contemplating the detailed circuitry. The ECG Processing mode represents conventional sensing. The Blanking mode represents the state of the switches during the time that sensing is disabled following a stimulus cycle.

The four phases of a pacing pulse, as depicted in FIG. 4, are separately listed in the table of FIG. 3 -Precharge, Stimulus, Active Postcharge, and Blanking. While it is true that the sense amplifier is blanked during the generation of a stimulus, the table entries for the Blanking mode apply only when the other entries do not, e.g., when sensing is to be disabled even in the absence of pacing.

The Passive Postcharge mode of operation is not ordinarily employed. In the event, however, that Active Postcharge is not desired, Passive Postcharge may be used, as will be described.

The Alert Drive High and Alert Drive Low modes of operation have already been described. The last two modes are similar and have to do with sensing functions. For example, periodically, e.g., ten times per second, a sensor associated with the patient's respiration may be interrogated. See, e.g., U.S. Pat. No. 4,702,253, entitled "Metabolic-Demand Pacemaker" issued on Oct. 27, 1987. Two different modes of operation are set forth in the table of FIG. 3 because the drive for the sensor may be through the case or the ring, and one of switches 1 or 2 is closed for this purpose.

Returning to the general description of the circuit of FIGS. 2A and 2B, the resistor network at the left of FIG. 2B is a standard R-2R ladder type network, with standard binary weightings. The network serves as an attenuator and thus controls sensing sensitivity. An 8-bit register (not shown) is set by the microprocessor to control the sensitivity, and the 8 switches in the ladder network have their positions controlled by the bits in this register. The sensitivity can be programmed by the physician, or it can be adjusted automatically by the microprocessor. In general, if the sensitivity is too low, a heartbeat may not be sensed; if the sensitivity is too high, noise may be erroneously interpreted as a heartbeat. Automatic sensitivity adjustment has no bearing on the present invention, and the attenuator of FIG. 2B is shown only because it is included in the integrated circuit in which the subject invention is implemented.

In FIG. 2B, there are three capacitors 54, 56 and 60, and resistor 58, all of which are external components. These elements are connected between three pins, PCMP_IN (positive comparator input), NCMP_IN (negative comparator input), and FIL_IN (filter input). In our copending application entitled "Combined Pacemaker Delta Modulator and Bandpass Filter," filed on even date herewith, these four external components are described. The four components and the attenuator output impedance function as a standard bandpass filter, as usually found in a pacemaker sense amplifier, and also at the heart of a delta modulator. The capacitors are external because they are too large to be integrated. Resistor 58 is also an external component because this allows greater control over its value.

In the illustrative embodiment of our invention, a form of delta modulation is utilized. The Q output of flip-flop 52, extended to node ANLG_CMP, is a two-level signal which is derived from the signal at the tip lead after attenuation by the ladder network. The input signal is applied to the plus input of comparator 50. The output sequence follows the input signal in the sense that the output represents a 1 when the input is increasing, and it represents a 0 when the input is decreasing. When the input is not changing, the output bits alternate in value. The technique of delta modulation in general is described in Money et al U.S. Pat. No. 4,466,440 which issued on Aug. 21, 1984. References may also be made to Money et al U.S. Pat. Nos. 4,448,196 which issued on May 15, 1984; 4,509,529 which issued on Apr. 9, 1985; and 4,527,133 which issued on July 2, 1985.

The input signal which is operated upon by a delta modulator can be reconstructed by causing a fixed-size step to be taken for each bit sample, the direction of the step depending upon the bit-sample value. As long as the delta modulator operates at a fast enough rate, the reconstructed signal will follow the input signal. Before proceeding with a description of the subject invention, the delta modulator shown on FIG. 2B will be described.

The heart of the delta modulator is the comparator 50, flip-flop 52, and two oppositely-poled current sources 38 and 40 connected between the negative and positive voltage supplies. The outputs of the flip-flop control switches 46 and 48. (Although not shown, it is possible to disable both switches by including a control gate in lines 42 and 44; these lines are symbolic only, and represent the flip-flop control over gates 46 and 48.) When switch 46 is closed, current flows up through constant-current source 38; when switch 48 is closed, current flows down through constant-current source 40.

The operation of a delta modulator can be best understood by first considering a different circuit, one in which the input signal from the attenuator is applied through capacitor 54 to the minus input of comparator 50, as shown, but with the plus input of the comparator being connected to a reference potential and otherwise disconnected from the circuit. Suppose, for example, that the input signal starts to decrease from some quiescent level. This tends to cause the potential at the minus input of the comparator to fall, and the output of the comparator goes high. The D input of flip-flop 52 is thus high, and the next 32K clock pulse causes the Q output of the flip-flop to go high. Switch 48 closes and current flows from source 40 to the left through capacitor 54. This tends to restore the potential at the minus input of the comparator to the reference level. In a similar manner, switch 46 closes to control a left-to-right current flow through the capacitor when the input signal increases from a quiescent level and the output of comparator 50 goes low to reset flip-flop 52. The state of the flip-flop is controlled in accordance with the current bit sample. Since the two outputs of the flip-flop control current flows from respective current sources, the output of the comparator not only represents a bit sample indicative of the manner in which the input signal is changing, but it also controls the current sources as required.

The minus comparator input is a virtual ground. It is maintained by the operation of feedback at the potential of the reference potential connected to the positive comparator input. Capacitor 54 is charged and discharged by the current sources so that the potential at the output of the attenuator has added to it or subtracted from it a capacitor potential such that the resulting level at the minus input of the comparator equals the reference potential. If a steady-state condition has been achieved, with alternating 0 and 1 bit samples appearing at the ANLG_CMP output node, and then there is a sudden change in the potential at the output of the attenuator, a number of bit samples of the same value will be generated until the capacitor has charged or discharged to an extent which compensates for the change at the output of the attenuator. The number of bit samples of constant value at the output of the delta modulator thus represents the magnitude of the change in the input signal, with the value of the output bits representing the direction of the change.

Instead of connecting the plus input to a reference potential as just described, however, we connect the plus input of the comparator to the input. Also, we connect capacitors 56 and 60, and resistor 58, across the inputs of the comparator. Most pacemakers and sense amplifiers have a bandpass filter consisting of two capacitors and two resistors. But the typical bandpass filter also includes an amplifier. In order to achieve a filter Q value greater than 1, either inductors must be used or an amplifier is necessary. A delta modulator also requires an amplifier and a capacitor. As far as the circuit of FIG. 2B is concerned, there is no savings in components since a delta modulator (requiring one capacitor) and a filter (requiring two capacitors and two resistors) would still require the same number of components shown in the drawing—three capacitors and two resistors. The savings is in the use of a single amplifier, comparator 50, instead of the two which would otherwise be required—one for the delta modulator and the other for the filter. The main advantage of achieving both delta modulator and filter functions with the use of a single active device is that less power is required to operate the pacemaker.

As far as the delta modulator is concerned, the details of its operation are not necessary for an understanding of the present invention. In fact, the circuit of FIG. 2B may be thought of in general terms as comprising an attenuator followed by a delta modulator. All that has to be known about the circuit is that switches 19 and 20 are both open at all times other than during sensing, as shown in the table of FIG. 3. This is done to prevent a change in the voltage across the capacitors, the delta modulator thus serving as a sample-and-hold circuit during blanking and whenever else the activity which is to take place is other than standard sensing.

Figure 5:
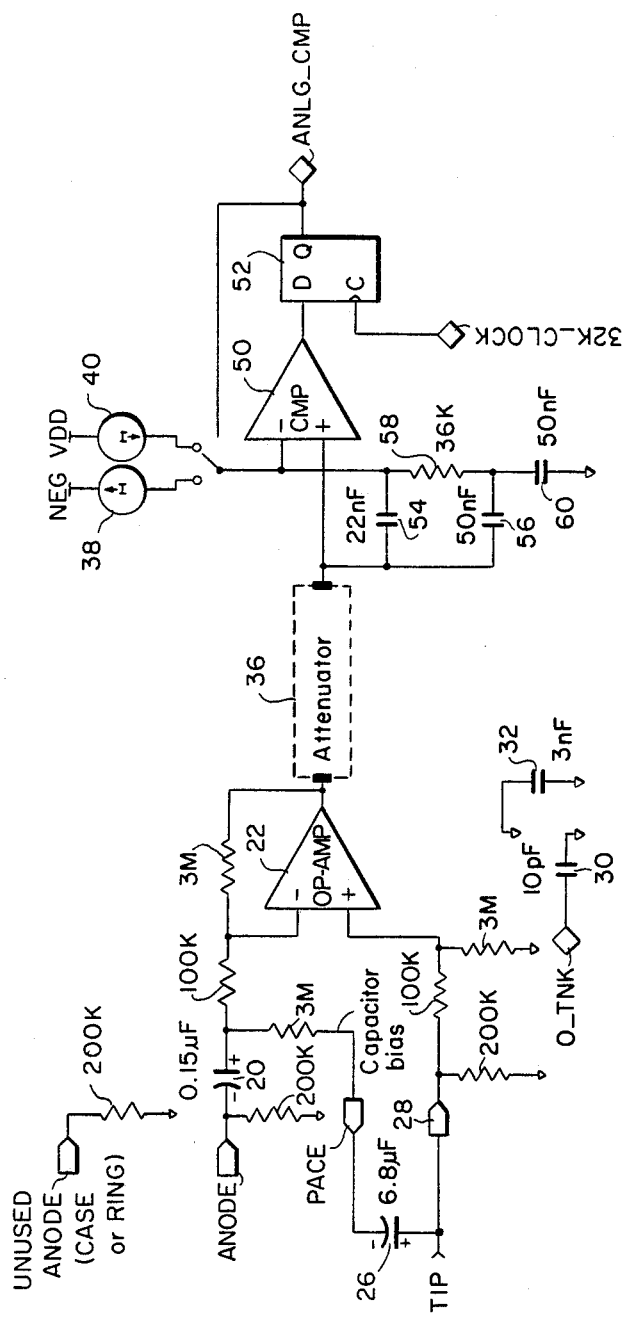
FIGS. 5–10 depict the operative components of the circuit of FIGS. 2A and 2B which are involved during different phases of the system operation, and will be helpful in understanding the system operation by focusing attention on only those elements whose understanding is necessary in each case.

What goes on during the ECG Processing mode is depicted in FIG. 5. The format of FIG. 5 is followed in the other figures. Only those components are depicted which are important for an understanding of the operation being described. [The delta modulator itself is shown as having a single switch for connecting either of the current sources to capacitor 54 for the sake of simplicity. Similarly, the attenuator at the left of FIG. 2B is shown as a block 36 in FIG. 5.] With respect to the CASE and RING pins of FIG. 2A, they are shown in FIG. 5 in a different form. One of them serves as the anode and the other is what can be termed an "unused anode." The case or the ring is the anode in each case, depending upon the positions of switches 3 and 4. Referring to FIG. 3, it will be noted that during ECG Processing both of switches 1 and 2 are open. Similarly, both of switches 5 and 6 are closed. As seen in FIG. 2A, each of the two possible anodes is thus connected through a 200K resistor to reference ground. Which of the two anodes is connected to the PA_REF pin depends upon which of switches 3 and 4 is closed. As indicated in FIG. 3, in the case of unipolar sensing, in which the case serves as the anode, switch 3 is closed and switch 4 is open. On the other hand, with bipolar sensing, switch 4 is closed and switch 3 is open. In either case, the effective anode is connected through a 200K resistor to reference ground, and to capacitor 20. This 200K resistor, and the 200K resistor connected to tip pin 28 in FIG. 2A, keep the electrodes from drifting more than a few millivolts from ground potential.

Operational amplifier 22 is arranged as a standard differential circuit with an AC coupling capacitor 20, but with one important difference. Because of the 3M resistor connected between the output of the amplifier and the minus input, and the provision of a 100K resistor at the input, the gain of the amplifier is 30. The plus input of the amplifier is similarly provided with a 100K resistor and a 3M resistor connected to ground. In this standard configuration, if the same potential change occurs at the left end of each of the 100K resistors, there will be no change in the output of the amplifier. What is unusual about the circuit of FIG. 5 is the 3M resistor which is connected between the PACE pin and capacitor 20. There is some offset voltage between the plus and minus inputs of operational amplifier 22. Current flows up through capacitor 26 in FIG. 5 until the capacitor charges to this offset voltage. (The capacitor actually charges to the offset voltage plus 1/31 times the tip voltage due to the voltage divider relationship of the resistors connected to the plus input. A potential of 1/31 of the tip voltage is typically a few microvolts and can be ignored. The reason for maintaining the offset voltage across the capacitor will become apparent below.

Aside from this unconventional connection of capacitor 26, the circuit operation is relatively straightforward. A differential amplifier circuit is used to derive an electrogram signal which is then attenuated; after attenuation, the delta modulator operates on the signal in a manner that, insofar as the subject invention is concerned, is conventional.

It should be noted that in accordance with the table of FIG. 3, during ECG Processing switch 11 is closed; this allows the tip to be connected to the plus input of operational amplifier 22 so that sensing can take place. Switch 13 is closed to connect ramp capacitor 32 to reference ground. This is shown in FIG. 5. The capacitor is held discharged in preparation for the generation of a ramp which will in turn control the shape of the precharge pulse. Switches 17 and 18 are both closed so that capacitor 30 is connected between reference ground and the 0_TNK potential. Capacitor 30 serves as a charge pump, as will be described, and initially it is held at the 0_TNK potential until it is needed.

Figure 6:
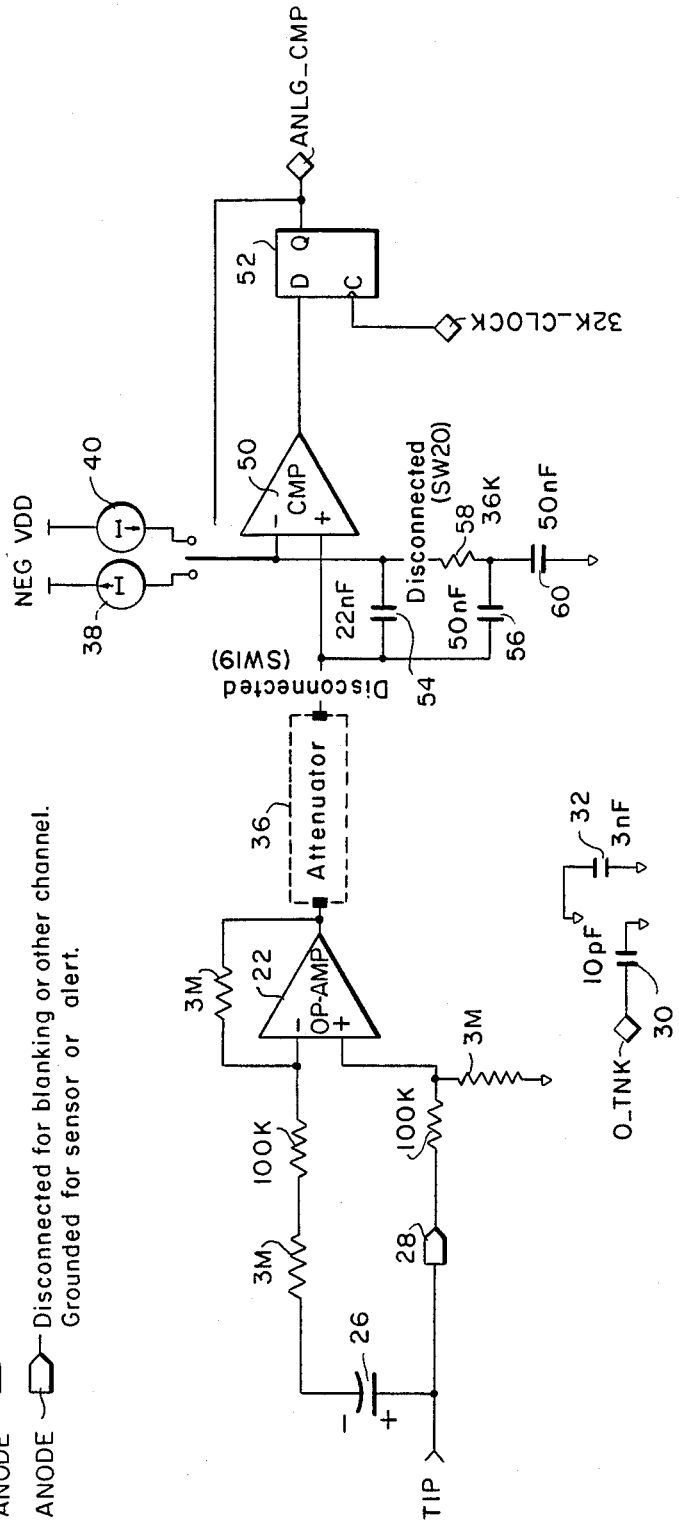

Referring to the table of FIG. 3, the next mode of operation is that of Blanking, and this mode is shown in FIG. 6. Because switch 19 is open, the delta modulator is in effect disconnected from the attenuator. Because switch 20 is open, the delta modulator capacitor potentials are simply held. It should be noted that neither of current sources 38 and 40 is shown as being connected to capacitor 54 during blanking. Although flip-flop 52 continues to be clocked, neither current source is connected to the capacitor. (It will be recalled that in connection with control lines 42 and 44 of FIG. 2B, it was mentioned that both of switches 46 and 48 could be held open.)

Although the drawing of FIG. 6 is designed to show what happens during blanking, the anode connections are labelled so that the alert and sensor modes are also depicted. During blanking, all of switches 1 through 6 are open and thus the two possible anodes are disconnected from the circuit. Depending upon whether a unipolar or bipolar lead is used, one of the two possible anodes is disconnected altogether. But even the other anode is also disconnected when sensing is blanked. The indication "or other channel" in the label for the operative anode is meant to imply that if a dual-chamber pacemaker is constructed in accordance with the principles of the invention, the anode associated with one chamber is blanked even when the other channel is paced. The anode label in FIG. 6 also states, that the anode which is used is grounded during alert and sensor functions. This results from one of switches 1 or 2 being closed, as indicated in the table of FIG. 3; a return path for the current used for the alert or sensor function is thus provided. (During the alert mode, switch 1 is closed so that the current return is through the case. The piezoelectric crystal used for the alert tone is mounted on the inside of the case, and that is why the case is used for the current return. In the sensor mode, however, the return path can be through the case or the ring. Reference may be made to application Ser. No. 787,125 referred to above. The ring is in the heart, and use of the ring as the anode allows better measurement of minute volume. If all that is desired is a measurement of the respiratory rate, however, it is more advantageous to use the case as the anode.)

During blanking, ramp capacitor 32 is still connected at both ends to reference ground, and the 0_TNK potential still appears across pump capacitor 30. When the system is blanked, potential changes at the tip are reflected at the output of amplifier 22. However, they have no effect on the system operation because sensing is blanked. Capacitor 26 remains charged to the offset voltage of amplifier 22.

Figure 7:
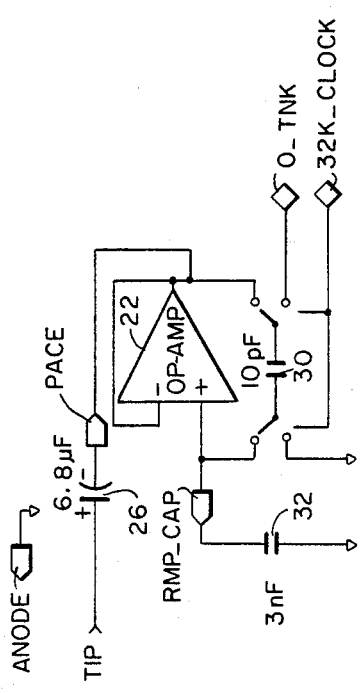

In the event a heartbeat is not detected by the end of the conventional escape interval, a pacing stimulus is generated. The three phases of the stimulus are shown in FIG. 4. The first phase is known as precharge, and the equivalent circuit during this phase of operation is shown in FIG. 7. Referring to FIG. 2A and the table of FIG. 3, one of switches 1 or 2 is closed so that the operative anode is connected to ground. Because switch 10 in FIG. 2A is closed, the resistor in the feedback path of amplifier 22 is shorted out. That is why the output of amplifier 22 in FIG. 7 is shown as being connected directly to the minus input. With switch 12 closed, the ramp capacitor 32 is connected between the plus input of the amplifier and ground. Also as depicted in the table of FIG. 3, switch 14 is closed so that capacitor 26 is connected to the output of the amplifier. Insofar as understanding the configuration of FIG. 7 is concerned, there remains to consider switches 15–18. As indicated in the table of FIG. 3, switches 15 and 16 are closed when switches 17 and 18 are open, and vice versa. The two pairs of switches change state under control of the 32K clock. Referring to FIG. 2A, it will be noted that with switches 17 and 18 closed, the pump capacitor is connected between the 0_TNK potential and ground. When switches 15 and 16 are closed, the capacitor is connected between the plus input of the amplifier and the output.

When the pump capacitor 30 is connected between ground and the 0_TNK node, the right side of the capacitor negatively (0_TNK is a negative potential). When charges the various switches cycle so that the capacitor is connected across the operational amplifier as shown in FIG. 7, the amplifier itself functions as a unity gain buffer since the output is connected to its minus input. Current flows through capacitor 30 from right to left, and down through ramp capacitor 32 to charge it positively. The current discharges pump capacitor 30, and charges the ramp capacitor until the pump capacitor is discharged. All of the charge on the pump capacitor is transferred to the ramp capacitor. Assuming that the 0_TNK potential is across a 6.8 uF capacitor, the full voltage is transferred to the pump capacitor. But the potential transferred to the ramp capacitor is inversly proportional to the relative capacitances of the ramp and pump capacitors. With the magnitudes shown, each step in the ramp is 1/300 of the 0_TNK potential. The step size remains substantially constant. The slope of the ramp depends upon both the rate at which the steps are applied, i.e., the 32K clock, and the step size.

The ramp potential which develops across capacitor 32 is buffered by amplifier 22 so that a positive potential is extended through capacitor 26 to the tip electrode. The duration of the precharge pulse is determined by the microprocessor. For each kind of lead, the precharge period can be determined by laboratory testing; the surface capacitance of an electrode varies with the material of which it is made and how that material has been treated. The stimulus of FIG. 4 can be applied over any lad in question to a saline solution. By converting the ANLG_CMP pulse sequence back to an analog signal, the precharge duration can be adjusted to give a minimal potential on the lead following the 8-millisecond postcharge interval to be described below. The postcharge duration is arbitrarily selected at 8 milliseconds, since this is short enough to allow the evoked signal to be sensed. With a postcharge duration of 8 milliseconds, a typical precharge period is around 3 milliseconds. (It is to be understood that the various phases of FIG. 4 are not shown to scale.)

The operational amplifier during the precharge mode of operation reproduces the ramp potential which develops across capacitor 32, but it does so with a low output impedance so that current is driven into the tip lead. Capacitor 26 must be able to withstand a reverse voltage of about three volts; with a VDD supply of 2.8 volts, the maximum operational amplifier output is less than three volts. Initially, there is an offset potential across capacitor 26, as described in connection with FIG. 5. The offset potential may be of either polarity. The voltage across the capacitor may change polarity as the capacitor charges during the precharge phase.

With a programmable pacemaker, one of the parameters which a physician may be allowed to control is the duration of the precharge (although this is not shown in the drawing). With telemetry, the physician is able to observe the electrogram signal which is sensed. The physician may gradually reduce the pacing pulse amplitude as he observes the sensed signal until capture is lost. At that point, what he observes following the postcharge period is the artifact which is sensed 8 milliseconds after the generation of a stimulus. The precharge interval may then be adjusted so that the artifact is minimized. It is also contemplated that the entire sequence can be automated so that the pacemaker automatically adjusts the duration of the precharge period. As will be described, the particular circuitry of our invention allows for automatic charge balancing, no matter what the pacing pulse amplitude, i.e., no matter what the magnitude of the 0_TNK potential. But this by itself does not eliminate the artifact following the postcharge period. What is necessary for this is that the charges delivered during the two positive phases have a ratio such that the potential at the point source is zero. It is expected that one day mechanisms will be developed for allowing the pacemaker to automatically adjust the relative charge levels delivered during the two positive phases to enhance sensing of an evoked signal following the postcharge phase.

Figure 8:
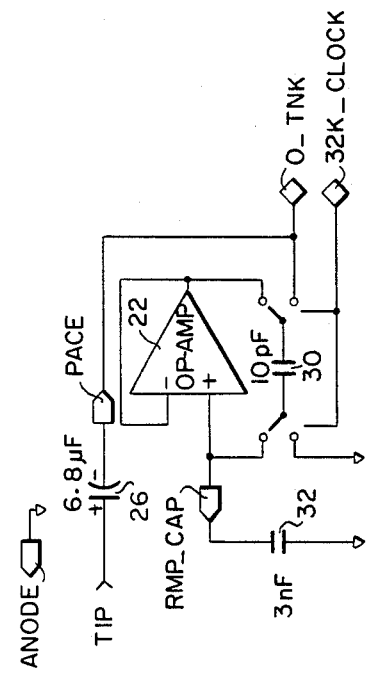

The circuit operation during the stimulus phase is shown in FIG. 8. Referring to the table of FIG. 3, it will be observed that switch 8 is now closed instead of open, and switch 14 is open rather than closed. Referring to FIG. 2A, the opening of switch 14 disconnects the output of the operational amplifier from the tip lead, and the closing of switch 8 connects the capacitor across which the 0_TNK potential is developed to output capacitor 26. The 0_TNK capacitor now discharges to generate the negative stimulus. During the course of the pulse, the capacitor discharges slightly, as is known in the art, and it is for this reason that the negative stimulus in FIG. 4 is shown decreasing in amplitude during its approximately 0.5-millisecond duration. This tapering of the amplitude of the pulse could be minimized by using a capacitor larger than the conventional 6.8 uF capacitor which is typically used. However, a larger capacitor would require more volume. Also, with a larger capacitor it would take longer to change the 0_TNK potential if the microprocessor decides that the pacing pulse amplitude requires change.

It should be noted that switches 15-18 still generate a ramp voltage across capacitor 32. It is totally unimportant, however, because the output of amplifier 22 is no longer connected to the PACE pin.

Figure 9:
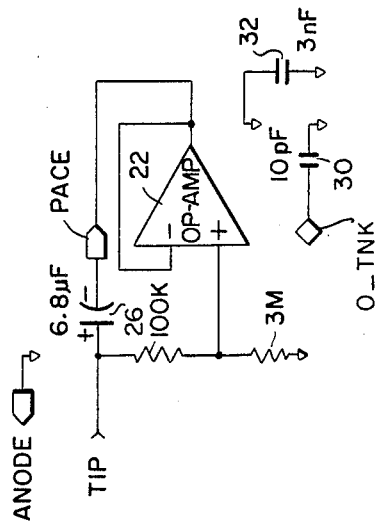

The active postcharge phase is shown in FIG. 9. Switch 14 is closed once again so that the output of amplifier 22 drives the tip lead. The amplifier is now used to generate the third phase, a positive pulse, and the amplifier output must be connected to the PACE pin. Switch 8 is no longer closed, so the 0_TNK potential no longer drives the tip lead. With switch 11 closed, the plus input of the amplifier is connected to the junction of 3M and 100K resistors, as depicted in FIG. 9. Finally, capacitors 30 and 32 are restored to the quiescent conditions, with the ramp capacitor being completely discharged and the pump capacitor having the 0_TNK potential placed across it in preparation for another cycle. It is the circuit of FIG. 9 which requires the closest scrutiny.

Figure 10:
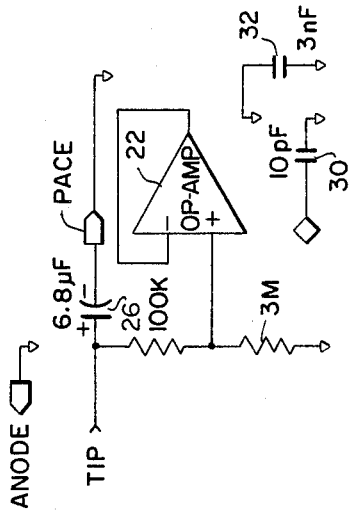

Referring to the table of FIG. 3, during the active postcharge switch 10 is closed so that the output of amplifier 22 is connected to the minus input. Switch 11 is closed so that the tip is connected through a 100K resistor to the plus input of the amplifier. The other switches which are closed maintain the potentials across capacitors 30 and 32 at their quiescent levels. Capacitor 26 forces charge balancing, as comparable capacitors have done in the prior art, by virtue of the fact that there can be no net current which flows through the capacitor and thus the tip lead. (The capacitor is also a safety factor because it prevents DC from being applied to the heart, something which would otherwise be fatal in the event of certain malfunctions of the integrated circuit.) In the prior art, in order to speed up the dissipation of charges stored in body tissues, following the generation of a negative stimulus the right side of capacitor 26 might be connected to ground. In fact, this is precisely what is shown in FIG. 10 for what is termed passive postcharge. In the event an active postcharge is not desired, as shown in the table of FIG. 3 switch 9 is closed rather than switch 14. Referring to FIG. 2A, this causes the right side of capacitor 26 in FIG. 10 to be connected to ground rather than to the output of operational amplifier 22 as in FIG. 9. During active postcharge, however, it is the voltage across the capacitor which drives the operational amplifier to not only discharge the capacitor, but also to dissipate charges remaining in body tissues.

The left side of the capacitor is connected through a 100K resistor to the plus input of the amplifier. The resistor is necessary for safety purposes; it limits the current which can be delivered to the tip electrode even if the plus input of the amplifier is shorted to the typically 2.8-volt supply. (The current is further limited by the 200K resistors which couple the anodes to ground through switches 5 and 6 during normal ECG processing; switches 1 and 2 are deliberately kept open so as not to short the case and the ring to ground.) Referring to FIG. 9, the 100K and 3M resistors form a voltage divider so that 30/31 of the capacitor voltage appears across the inputs of the operational amplifier. The output of the amplifier is driven positively and current flows to the left through the capacitor and the tip lead. The current waveform is substantially independent of the body impedance through which the current flows.

The output of the operational amplifier is connected to the PACE node through switch 14, even though the switch is not shown in the drawing of FIG. 9. The switch typically as an impedance of about 100 ohms. The impedance of the body seen by the tip electrode is similarly in the order of a few hundred ohms. (That is why the current flow through capacitor 26 is into the body, and not through the 100K resistor.) At the start of the active postcharge, the voltage at the tip lead rises instantaneously as shown in the waveform of FIG. 4; the actual step in the potential depends upon the ratio of the body impedance to the switch impedance. As shown in FIG. 4, the peak positive potential at the start of the postcharge phase is slightly higher than the peak of the ramp at the end of the precharge phase. However, depending on the ratio of the impedances, and the magnitude of the charge delivered during the precharge phase, the postcharge peak could be smaller than the precharge peak.

In any event, the current which flows during the active postcharge period enters the right side of the capacitor and exits the left side. Current stops flowing when an equilibrium condition is reached. At this time, the potential across the capacitor will be equal to the offset voltage across the two inputs of the amplifier. This is exactly the same condition that was described above in connection with the ECG processing diagram of FIG. 5. It will be recalled that while the system is sensing cardiac activity, capacitor 26 is charged to the offset potential. What this means is that at the end of the postcharge phase, the capacitor has the identical charge that it had just before the precharge phase. This, in turn, means that charge balance has been achieved. More important, the charge balance has been achieved very quickly, because during the balancing process the potential across the capacitor causes the amplifier to actively drive the potential in the opposite direction.

It should be noted that with an impedance for switch 14 of 100 ohms, the time constant of the charging circuit, taking into account the fact that capacitor 26 has a magnitude of 6.8 uF, is only 0.68 millisecond. This means that well before the postcharge duration of 8 milliseconds, charge balancing is achieved. When passive postcharge is employed, the recharge interval is much longer, as in the prior art. Typically, it requires 50-150 milliseconds before sensing becomes reliable once again. This should be compared with the 8-millisecond active postcharge period of the invention. The largest part of the evoked potential following the generation of a negative stimulus occurs during the first 30 milliseconds following the stimulus. Thus, use of the invention allows most of the evoked potential to be sensed.

In the prior art, in the context of only a single positive pulse (following the negative stimulus) being provided, it was suggested to return a capacitor, such as the right side of capacitor 26, to a positive supply. The problem with this is that there is no way of knowing how long the connection should be maintained. It is not enough to make the positive and negative pulse phases equal in duration because the impedance of the body tissues is generally lower during the positive phase than during the negative phase; thus, the charges which would flow in the two directions while the capacitor is connected to two supplies would not necessarily be equal, and it would take longer until the remaining charges dissipate. In the invention, on the other hand, an active drive is provided to control the balancing until, and only until, the balancing is achieved; it is known when the charge has been balanced because the capacitor drives the postcharge phase only until it is in exactly the same condition that it was before the precharge phase. What is more, the postcharge phase takes place while a small time constant characterizes the output circuit, so that reliable sensing can resume well before the evoked potential has disappeared.

It should now be apparent why capacitor 26 in FIG. 5 is connected in the rather strange configuration referred to above. The configuration shown in FIG. 5 insures that the potential across the capacitor is equal to the offset potential of amplifier 22. The only reason for developing this potential across the capacitor during ECG processing is that this is the potential which develops across the capacitor when postcharge is completed. This feature, however, is not critical, especially if the offset potential of the operational amplifier is low. Perhaps the most important aspect of the invention is the provision of the standard coupling capacitor in the feedback path of the operational amplifier so that the capacitor is rapidly driven, with all of the current flowing through the capacitor and the body. In this way, the driving current stops automatically when the capacitor is returned to its quiescent condition, and because all of the current flows through the body, the body has also been returned to its quiescent condition.

Another important feature of the invention is that the precharge current varies with the magnitude of the 0_TNK potential and so does the amplitude of the stimulus. As described above in connection with the precharge drawing of FIG. 7, the 0_TNK potential determines the amplitude of the precharge pulse. Similarly, as described in connection with the stimulus drawing of FIG. 8 and the waveform of FIG. 4, the 0_TNK potential determines the amplitude of the negative stimulus. Thus, varying the 0_TNK potential does not affect the charge balancing at all. The charge delivered during the precharge phase is proportional to the charge delivered during the stimulus. In general, it is sufficient if the charges are substantially proportional to each other, that is, if the two charges are proportional to each other to within 10%. As described above, for reliable sensing to take place very shortly after the negative stimulus, it is not enough that the net charge be zero. What is also important are the relative amounts of charge in the two positive wavefronts. This is a function of the timing of the three phases in each cycle. The duration of the precharge pulse is controlled to maximize performance. The charge and timing relationships will thereafter not be affected by changing the 0_TNK potential because this potential determines the charges delivered during the first two phases in a proportional manner.

The invention is also applicable to biphasic pulses, in which there is an active postcharge pulse but no precharge pulse. In the prior art, the charge delivered during the postcharge period was dependent upon the impedance of the body. Because the body impedance varies, charge balancing could not be controlled during the active period. The coupling capacitor would always insure charge balancing, but a longer time would be required for it because there was no way for the circuit to know exactly when to stop the active postcharge, i.e., when charge balancing was achieved. In the circuit of the subject invention, however, even in the absence of a precharge pulse, active postcharge persists until, and only until, charge balance is achieved—substantially independent of the body impedance.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

We claim:

1. A pacemaker stimulus-generating circuit comprising an electrode, a coupling capacitor, and means for controlling an isolated stimulus cycle including means for causing a negative stimulating current to flow to said electrode through said capacitor, and means driven by the capacitor voltage for applying a subsequent positive current to said electrode through said capacitor until the capacitor voltage returns to its value prior to the start of the isolated stimulus cycle, said positive current applying means operating to apply a current which is a function of said capacitor voltage but which is substantially independent of the body load impedance to which said electrode is coupled.

2. A pacemaker stimulus-generating circuit in accordance with claim 1 further including means for generating a positive current flow through said capacitor and said electrode immediately prior to the flow of said negative stimulating current.

3. A pacemaker stimulus-generating circuit in accordance with claim 2 wherein during each cycle of operation the net charge delivered to said electrode is zero.

4. A pacemaker stimulus-generating circuit in accordance with claim 3 further including means for varying the amplitude of said negative stimulating current, and means for controlling the positive charge delivered to said electrode immediately prior to the flow of said negative stimulating current to be substantially proportional to the negative charge delivered during the flow of said negative stimulating current independent of said amplitude.

5. A pacemaker stimulus-generating circuit in accordance with claim 4 wherein the positive current flow immediately prior to the flow of said negative stimulating current is in the form of a ramp waveform.

6. A pacemaker stimulus-generating circuit in accordance with claim 5 wherein the amplitude of said ramp waveform and the amplitude of said negative stimulating current are substantially proportional to each other, and the duration of said ramp waveform is such that the after-potential at said electrode is minimized immediately after said subsequent positive current is applied.

7. A pacemaker stimulus-generating circuit in accordance with claim 5 wherein the amplitude of said ramp waveform and the amplitude of said negative stimulating current are substantially proportional to each other, and the duration of said ramp waveform is such that the after-potential at said electrode immediately after said subsequent positive current is applied is low enough to allow reliable sensing at said electrode of a heartbeat signal evoked by said negative stimulating current.

8. A pacemaker stimulus-generating circuit in accordance with claim 4 wherein the ratio of charges delivered to said electrode prior and subsequent to said negative stimulating current is such that the after-potential at said electrode immediately after said, subsequent positive current is applied is low enough to allow reliable sensing of a heartbeat signal evoked by said negative stimulating current.

9. A pacemaker stimulus-generating circuit in accordance with claim 3 wherein said positive current applying means includes an operational amplifier with said capacitor connected in the feedback path thereof, said operational amplifier causing a positive current to flow until the capacitor voltage is reduced sufficiently to support the offset potential which appears across the inputs of said operational amplifier.

10. A pacemaker stimulus-generating circuit in accordance with claim 9 further including means for controlling said operational amplifier to function as a sense amplifier, and means operative while said amplifier functions as a sense amplifier for simultaneously developing across said capacitor a potential which is equal to the potential which appears across said capacitor at the termination of said subsequent positive current flow.

11. A pacemaker stimulus-generating circuit in accordance with claim 3 wherein said positive current applying means includes an operational amplifier with said capacitor connected in the feedback path thereof.

12. A pacemaker stimulus-generating circuit in accordance with claim 11 further including means for controlling said operational amplifier to function as a sense amplifier.

13. A pacemaker stimulus-generating circuit in accordance with claim 12 further including means operative while said operational amplifier functions as a sense amplifier to develop a potential across said capacitor which equals the potential which remains across said capacitor at the termination of said subsequent positive current flow.

14. A pacemaker stimulus-generating circuit in accordance with claim 13 wherein said negative current and said positive currents have amplitude and time relationships such that the after-potential at said electrode immediately after said subsequent positive current is applied is low enough to allow reliable sensing at said electrode of a heartbeat signal evoked by said negative stimulating current.

15. A pacemaker stimulus-generating circuit in accordance with claim 3 wherein said negative current and said positive currents have amplitude and time relationships such that the after-potential at said electrode immediately after said subsequent positive current is applied is low enough to allow reliable sensing at said electrode of a heartbeat signal evoked by said negative stimulating current.

16. A pacemaker stimulus-generating circuit in accordance with claim 1 wherein said positive current applying means includes an operational amplifier with said capacitor connected in the feedback path thereof, said operational amplifier causing a positive current to flow until the capacitor voltage is reduced sufficiently to support the offset potential which appears across the inputs of said operational amplifier.

17. A pacemaker stimulus-generating circuit in accordance with claim 16 further including means for controlling said operational amplifier to function as a sense amplifier, and means operative while said amplifier functions as a sense amplifier for simultaneously developing across said capacitor a potential which is equal to the potential which appears across said capacitor at the termination of said subsequent positive current flow.

18. A pacemaker stimulus-generating circuit in accordance with claim 1 wherein said positive current applying means includes an operational amplifier with said capacitor connected in the feedback path thereof.

19. A pacemaker stimulus-generating circuit in accordance with claim 18 further including means for controlling said operational amplifier to function as a sense amplifier.

20. A pacemaker stimulus-generating circuit in accordance with claim 19 further including means operative while said operational amplifier functions as a sense amplifier to develop a potential across said capacitor which equals the potential which remains across said capacitor at the termination of said subsequent positive current flow.

21. A pacemaker stimulus-generating circuit comprising an electrode, a coupling capacitor, and means for controlling an isolated stimulus cycle including means for generating a positive current flow through said capacitor and said electrode, means for causing a negative stimulating current to flow to said electrode through said capacitor, and means driven by the capacitor voltage for applying a subsequent positive current to said electrode through said capacitor until the capacitor voltage returns to its value prior to the generation of said positive current at the start of the isolated stimulus cycle, means for varying the amplitude of said negative stimulating current, and means for controlling the amplitude of said positive current flow immediately prior to the flow of said negative stimulating current to be a substantially fixed proportion of the amplitude of said negative stimulating current independent of said amplitude.

22. A pacemaker stimulus-generating circuit in accordance with claim 21 wherein the positive current flow immediately prior to the flow of said negative stimulating current is in the form of a ramp waveform.

23. A pacemaker stimulus-generating circuit in accordance with claim 22 wherein the amplitude of said ramp waveform and the amplitude of said negative stimulating current are substantially proportional to each other, and the duration of said ramp waveform is such that the after-potential at said electrode is minimized immediately after said subsequent positive current is applied.

24. A pacemaker stimulus-generating circuit in accordance with claim 22 wherein the amplitude of said ramp waveform and the amplitude of said negative stimulating current are substantially proportional to each other, and the duration of said ramp waveform is such that the after-potential at said electrode immediately after said subsequent positive current is applied is low enough to allow reliable sensing at said electrode of a heartbeat signal evoked by said negative stimulating current.

25. A pacemaker stimulus-generating circuit in accordance with claim 21 wherein the ratio of charges delivered to said electrode prior and subsequent to said negative stimulating current is such that the after-potential at said electrode immediately after said subsequent positive current is applied is low enough to allow reliable sensing of a heartbeat signal evoked by said negative stimulating current.

26. A pacemaker stimulus-generating circuit in accordance with claim 21 wherein said positive current applying means includes an operational amplifier with said capacitor connected in the feedback path thereof.

27. A pacemaker stimulus-generating circuit in accordance with claim 26 further including means for controlling said operational amplifier to function as a sense amplifier, and means operative while said amplifier functions as a sense amplifier for simultaneously developing across said capacitor a potential which is equal to the potential which appears across said capacitor at the termination of said subsequent positive current flow.

28. A pacemaker stimulus-generating circuit in accordance with claim 21 wherein said negative current and said positive currents have amplitude and time relationships such that the after-potential at said electrode immediately after said subsequent positive current is applied is low enough to allow reliable sensing at said electrode of a heartbeat signal evoked by said negative stimulating current.

* * * * *